(12) United States Patent
Zur et al.

(10) Patent No.: US 6,406,437 B1
(45) Date of Patent: Jun. 18, 2002

(54) METHOD AND APPARATUS FOR EFFICIENT HIGH-RESOLUTION VISUAL FIELD MAPPING

(75) Inventors: Dror Zur, Herzelia; Shimon Ullman, Rehovot, both of (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/686,604

(22) Filed: Oct. 11, 2000

(51) Int. Cl.[7] .............................................. A61R 13/00
(52) U.S. Cl. ...................................... 600/558; 350/200
(58) Field of Search ................... 600/558; 351/200–247

(56) References Cited

U.S. PATENT DOCUMENTS 4,995,717 A * 2/1991 Damato ...................... 351/224
5,946,075 A * 8/1999 Horn .......................... 351/246

* cited by examiner

Primary Examiner—Kevin Shaver
Assistant Examiner—Pamela L. Wingood
(74) Attorney, Agent, or Firm—Martin Fleit; Paul D. Bianco

(57) ABSTRACT

A micro-perimeter technique using a portable computer and a projector, and using two screening methods, multi-resolution static and bi-directional kinetic. The static method, as applied to a static test, starts with relatively low-resolutions, and only the unseen zones are selectively remapped under higher resolutions during successive iterations. The bi-directional kinetic method, as applied to a kinetic test, uses a response to a continuously moving target, and the unknown response delay is compensated for by an algorithm that merges the patient's response to measurements at the same visual location, but with opposite scanning directions. Offline visualization of the mapping results is performed automatically superimposed over the fundus image.

43 Claims, 9 Drawing Sheets

Phase 1: X Resolution – 2.0 degrees, Y Resolution – 2.0 degrees

```
              12.0              0.0            12.0

17.0                 0
                  0 0 0 0 0 0 0
                0 0 0 0 0 0 0 0
              0 0 0 0 0 0 0 0 0 0
              0 0 0 0 0 0 0 0 X 0
              0 0 0 0 X X X X X X
          0 0 0 X X X X X 0 0 0 0
              0 0 0 X X X X X 0 0
              0 0 0 0 X 0 0 0 0 0
              0 0 0 0 0 0 0 0 0 0
                0 0 0 0 0 0 0 0
                  0 0 0 0 0 0 0
                         0

17.0
```

Statistics of phase 1:
Elapsed time: 7:16 [min:sec]
Number of tested dots: 113
Number of tested dots seen at first illumination: 87
Number of tested dots seen at second illumination: 5
Number of tested dots not seen at all: 21
Number of dots covered before (not tested in this phase): 0
False positive errors: 0 out of 16 test cases
Fixation nasal losses: 14 out of 20 test cases
Fixation temporal losses: 19 out of 20 test cases
Fixation up losses: 19 out of 21 test cases
Fixation down losses: 19 out of 20 test cases
Fixation total losses: 71 out of 81 test cases

FIG. 2A

Phase 2: X Resolution - 1.0 degrees, Y Resolution - 1.0 degrees

```
                     12.0                    0.0                       12.0
        17.0                              o
                                  o o o o o o o o
                                o o o o o o o o o o o
                              o o o o o o o o o o o o o
                            o o o o o o o o o o o o o o o
                          o o o o o o o o o o o o o o o o o
                        o o o o o o o o o o o o o o o o o o o
                        o o o o o o o o o o o o o o X X X o
                      o o o o o o o o o o o o o o o o X 0 0 o o
                      o o o o o o o o 0 X 0 0 0 0 0 0 X X 0 0 0 0
                      o o o o o o o o 0 X X X X 0 X X X 0 0 0 0 0
                      o o o o 0 X X X 0 X 0 X X X X X 0 0 0 0 0 0
                    o o o o o X 0 X X X 0 X X X 0 X X X o o o o o o o
                      o o o o 0 0 0 X 0 X X X X X 0 X X X X o o o o
                      o o o o o o 0 X X X X X X X X X X X o o o o
                      o o o o o o 0 0 0 X X X X X X X X 0 o o o o
                      o o o o o o o o o X X X o o o o o o o o
        0.0             o o o o o o o o o X X 0 o o o o o o o o
                        o o o o o o o o o o o o o o o o o o o
                          o o o o o o o o o o o o o o o o o
                            o o o o o o o o o o o o o o o
                              o o o o o o o o o o o o o
                                o o o o o o o o o o o
                                  o o o o o o o o
                                        o
```

17.0

Statistics of phase 2:
Elapsed time: 10:22 [min:sec]
Number of tested dots: 115
Number of tested dots seen at first illumination: 30
Number of tested dots seen at second illumination: 14
Number of tested dots not seen at all: 71
Number of dots covered before (not tested in this phase): 326
False positive errors: 2 out of 31 test cases
Fixation nasal losses: 24 out of 26 test cases
Fixation temporal losses: 26 out of 26 test cases
Fixation up losses: 26 out of 27 test cases
Fixation down losses: 27 out of 27 test cases
Fixation total losses: 103 out of 106 test cases

FIG. 2B

THE LR RESULTS:
Phase 0: X Resolution - 0.5 degrees, Y Resolution - 1.0 degrees

THE RL RESULTS:
Phase 0: X Resolution - 0.5 degrees, Y Resolution - 1.0 degrees

THE LRRL RESULTS:
Phase 0: X Resolution - 0.5 degrees, Y Resolution - 1.0 degrees

METHOD AND APPARATUS FOR EFFICIENT HIGH-RESOLUTION VISUAL FIELD MAPPING

BACKGROUND OF THE INVENTION

1. Field of Invention

The present invention relates to an apparatus and method for high-resolution, low-cost perimetry, and more particularly, relates to an apparatus and method for high-resolution, low-cost perimetry for improved the static and kinetic visual filed mapping.

2. Prior Art

Visual field mapping (fundus perimetry) is a psychophysical test performed by projecting small light stimuli to different locations and different perimeters of the fundus. It is commonly used in the detection, diagnosis and evaluation of several retinal, optic nerve and brain diseases, such as glaucoma, retinitis pigmentosa and stroke. The most commonly used apparatus are the photopic Goldman device which uses a manual kinetic test,[1] and the photopic and scotopic Humphrey instrument which uses an automatic static test.[2-5] In the static method, a dot of light is flashed at random locations onto a visual field and the patient signals when he/she sees the flash. The patient adjusts fixation between each flash by a centrally presented target. This method allows for both screening and threshold mapping. In contrast, in the kinetic method, a dot of light moves in straight lines in the visual field, and the patient signals when the dot is visible and when it disappears. During each scan, the patient is required to maintain fixation. For example, in order to test the peripheral damage caused by glaucoma, it is common to scan twelve different radial lines, equally separated by 30°. However, this technique has the limitation of indeterminacy in the precise location at which the patient has signaled, since the response delay is unknown. Therefore, the kinetic test is considered rapid but imprecise,[1,6,7] and it is usually used for qualitative tests, such as depicting lines of equal sensitivity in the visual field.[2]

The conventional apparatuses described above are not suitable for mapping inside the macula region, since an accurate high-resolution mapping is required. The Goldman perimeter is limited by the problem posed by the patient's response delay and the fact that operator monitoring is done manually, while the Humphrey instrument has limitations imposed by its software implementation (the most common mapping resolution is 4°) and the resolution of the bulbs in its hemisphere. In addition, the patient's eye movements can cause significant errors at high-resolution of less than 1°.

Severe damage to the macula often results in eccentric fixation, which is unstable in comparison with normal fixation.[8-10] Studies on macular-damaged retinas have shown that more than 50% of mapping trials had a shift of up to 15 minutes of arc (0.25°) during a 400 msec flash, while 40% of trials had a shift of 1.5° or more during a 1000 msec flash.[11] Thus, the eye movements are significant enough, but still can be hardly detected by projecting to the blind spot (as it is done in the Humphrey device) since its radius is about 5°. Moreover, the blind spot's location is shifted under eccentric fixation, causing misplacement of the estimated blind spot's location.

The new generation of fundus perimeters enables the visualization of the retina with precise high-resolution mapping superimposed on it. The most sophisticated of them is the scanning laser ophthalmoscope (SLO).[6,7,9,12-22] The SLO uses two simultaneous laser beams, an invisible infrared beam for imaging the retina, and a visible red beam for perimetry. The SLO enables automatic kinetic and static studies with a resolution of 2 minutes of arc (0.033°). The operator can see the retinal image and the fixation target during the test, and can thus compensate online for significant eye movements.[9] The SLO and other advanced fundus perimeters are attractive for research, but they are still not in widespread practical use, mainly due to their high cost and cumbersome operation.

SUMMARY OF THE INVENTION

The present invention seeks to overcome the disadvantages and drawbacks of the prior art, as explained above, and provides a method and apparatus for high-resolution, low-cost perimetry, and more particularly, relates to an apparatus and method for high-resolution, low-cost perimetry for improved the static and kinetic visual filed mapping. The focus of the work leading to the present invention concerned mapping macular scotomas and checking the residual sight in them, by using common affordable tools. Thus, the main goal was to achieve low-cost high-resolution mapping with minimal eye movements error, and with results that can be automatically visualized on the fundus photograph.

The foregoing is is accomplished by the present invention by employing as the perimeter a portable computer and a projector, and using two screening methods, multi-resolution static and bi-directional kinetic. The invention as applied to a static test starts with relatively low-resolutions, and only the unseen zones are selectively remapped under higher resolutions during successive iterations. The invention as applied to a kinetic test uses a response to a continuously moving target, and the unknown response delay is compensated for by an algorithm that merges the patient's response to measurements at the same visual location, but with opposite scanning directions. Offline visualization of the mapping results is performed automatically superimposed over the fundus image.

Other and further objects and advantages of the present invention will become more readily apparent from the following detailed description of preferred embodiments when taken in conjunction with the appended drawings.

BRIEF DESCRIPTION OF THE DRAWINGS

FIGS. 2A and 2B are schematic representations illustrating two successive iterations of the multi-resolution static technique of the present invention.

DETAILED DESCRIPTION OF PREFERRED EMBODIMENTS

Figure 1A:
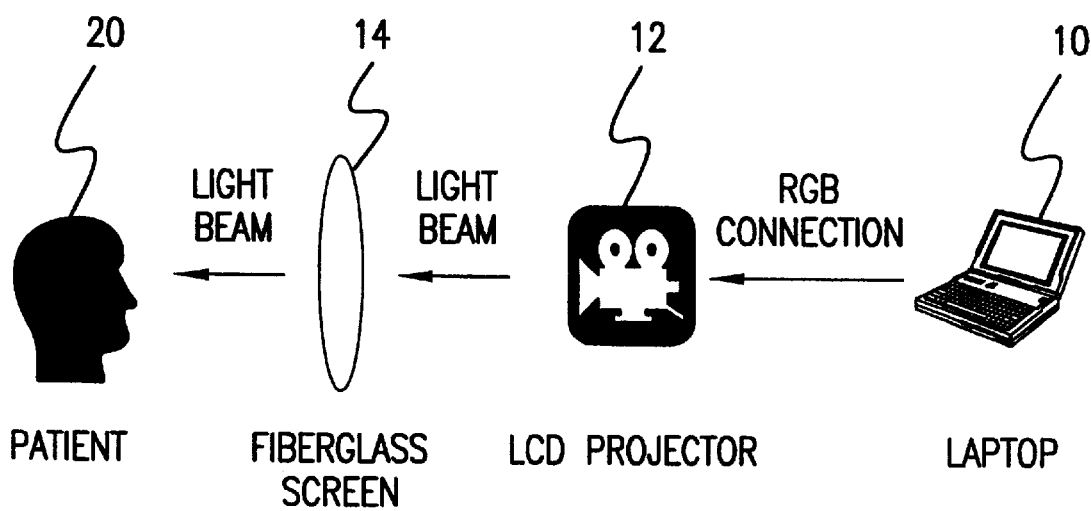
FIG. 1A is a schematic illustration showing the perimeter.

The present invention presents a method and apparatus to obtain a high-resolution low-cost perimeter, and in this detailed description of preferred embodiments describes improvements offered by two modes of operation, the static and kinetic visual filed mapping. As an example of the perimeter which may be used, it may consist of a portable computer and a projector, that may be operated using two screening methods, multi-resolution static and bi-directional kinetic. When using the static method, the static test starts with relatively low-resolutions, and only the unseen zones are selectively remapped under higher resolutions during successive iterations. When using the kinetic method, the kinetic test uses a response to a continuously moving target, and the unknown response delay is compensated for by an algorithm that merges the patient's response to measurements at the same visual location but with opposite scanning directions. Offline visualization of the mapping results is performed automatically superimposed over the fundus image.

In a specific series of tests, eight eyes were tested: four normal and four which had age-related macular degeneration (AMD). The visualization showed good correspondence between the mapping and the scotoma borders. There was some degree of inconsistency in the static test, probably due to random eye movements, which increased as visual acuity decreased. The kinetic test was usually shorter and more consistent and, therefore, more accurate and repeatable. The blur in perceiving some regions in the kinetic test suggests that it may be used as a higher sensitivity test.

The conclusions reached as a result of these series of tests were that the kinetic method proved superior to the static method as an accurate mapping, due to its faster and more consistent results. The implementation is considerably less expensive than using a scanning laser ophthalmoscope (SLO) and, except for online visualization, it provided results that in practice approached those of the SLO.

In greater details, the main features of the present invention include rapid, accurate, and repeatable high-resolution visual field mapping (micro-perimetry) by using multi-resolution static mapping, bi-directional kinetic mapping or high-sensitivity bi-directional kinetic mapping. The inventive multi-resolution static mapping method includes the steps of flashing a dot of light at random locations in the tested visual field, fixation adjustment between each flash using a centrally presented target, detecting whether or not the patient sees the flash, by the patient signaling "see" or "not see". Essentially, the dot of light that is flashed is stepped from point to point, but not necessarily in order, but rather in random fashion. The method starts with relatively low-resolutions in a first phase, in order to rapidly obtain indications of the unseen regions, and with successive iterations remaps only the unseen regions under higher resolutions. The final results are presented with uniform resolution (see FIG. 2). Therefore, the highest tested resolution (regions which were tested merely with lower resolution are decomposed to the highest resolution, with the decomposed values being identical to the original value). A screening and threshold mapping can take place. In screening, only one intensity is used whereas in threshold mode, the intensity is varied from a low value to a high value to discover the threshold between "see" and "not see" for the intensity range. In the threshold mapping, the iterations are repeated for each tested intensity. Regions, which were unseen at higher intensity, or seen at lower intensity, are skipped. Acceleration is achieved by first testing with the lowest and highest intensities, and then testing with the intermediate intensities.

Figure 3:
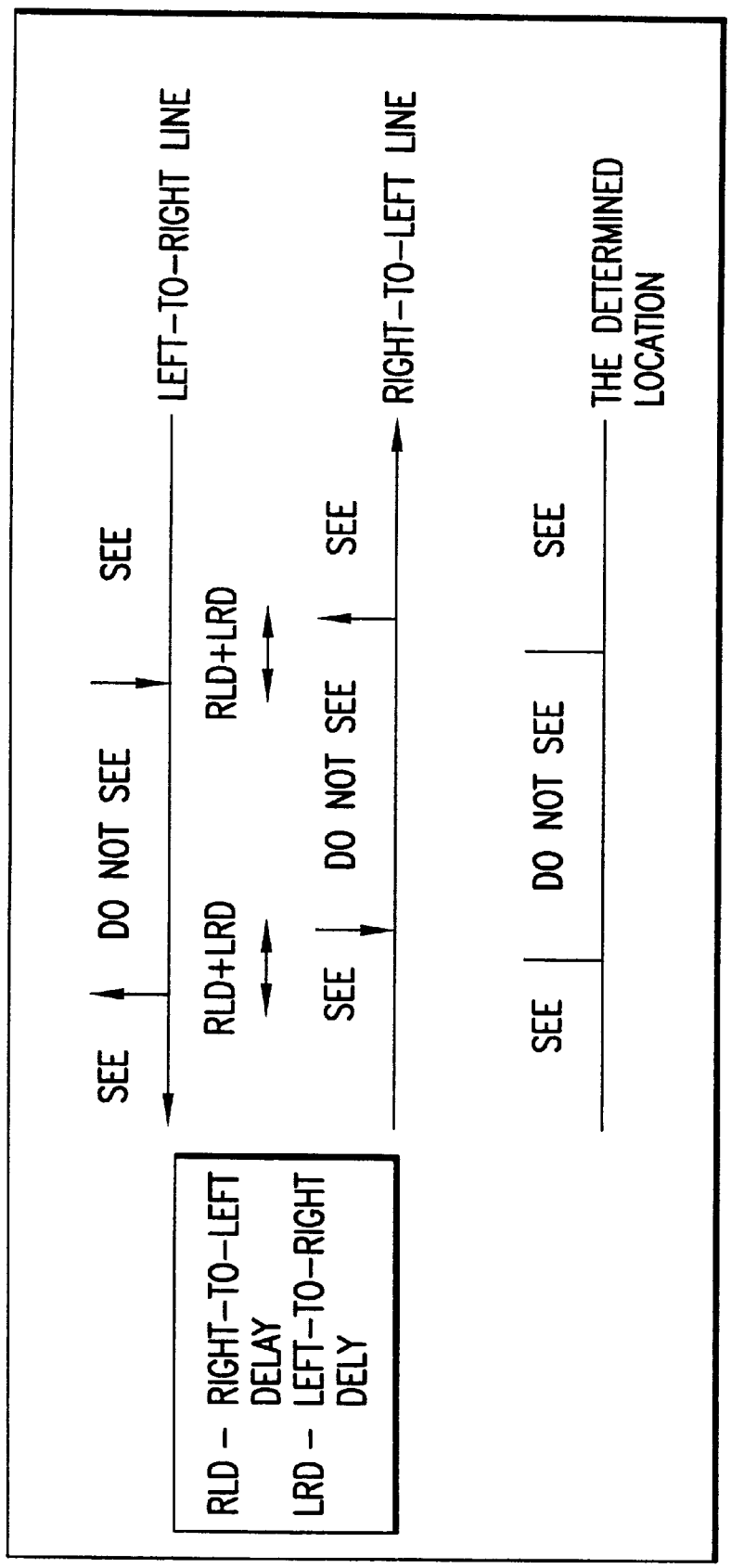
FIG. 3 is a schematic illustration showing how the present invention solves the response delay of the kinetic visual field mapping.

The bi-directional kinetic mapping method of the present invention includes the steps of moving a dot of light in lines at the tested visual field, maintaining patient fixation during each line scan, detecting patient signals when the dot becomes visible or disappears, computing the patient's response delay by merging the patient's response to scans at the same visual location but with opposite scanning directions (each tested visual location is scanned with two opposite directions), determining the actual location of the patient's signal at a point between each two corresponding opposite signals (see FIG. 3). There are two types of presentation for the results d. In one form of presentation, "topographic lines" are derived showing the connecting lines of neighboring points of the same level of perceptual vision transition. In the other type of presentation which is called "discretization" and is a "static-like" presentation, the actual points with their perception values are presented. The movement of the dot of light and the mapping may be either rectilinear or polar (radial). The discretization presentation is usually in the form of a rectilinear display (see FIG. 4). The topographic lines, usually in the form of polar display, produces a map of the transition between "see" and "not see" signals. The bi-directional kinetic mapping according to the invention, includes screening and threshold mapping. The screening takes place using one selected intensity whereas for the threshold mapping, the scans are repeated for each tested intensity. Segments or points, which were unseen in higher intensity, or seen in lower intensity, are skipped. Acceleration is achieved by first testing with the lowest and highest intensities, and then testing with the intermediate intensities.

Another feature of the present invention is the inclusion in the method and apparatus of a correction of the influence of eccentric fixation under central disorder. This is accomplished by finding, in advance, the eccentric fixation retinal point (for example by using slit-lamp and red laser beam, according to known-technology), computing, in advance, the distance and orientation of the eccentric fixation point from the normal fixation point (the center of fovea), and displacing each tested location in the visual field by the computed distance and orientation.

The methods of the invention utilize offline visualization of the mapping results over the retinal photograph using the computer-microprocessor by finding, in advance, the fixation retinal point (for example by using slit-lamp and red laser beam), scanning, in advance, the retinal photograph, into the computer, including its scale, signing the fixation point on the retinal computer image, offline graphical drawing of the test result over the retinal image, aligning it with the fixation point (the orientation is assumed to be fixed for all the subjects, since the patient's head is stabilized). See FIG. 5 and 6 for the visualization of the static and kinetic results.

Figure 1B:
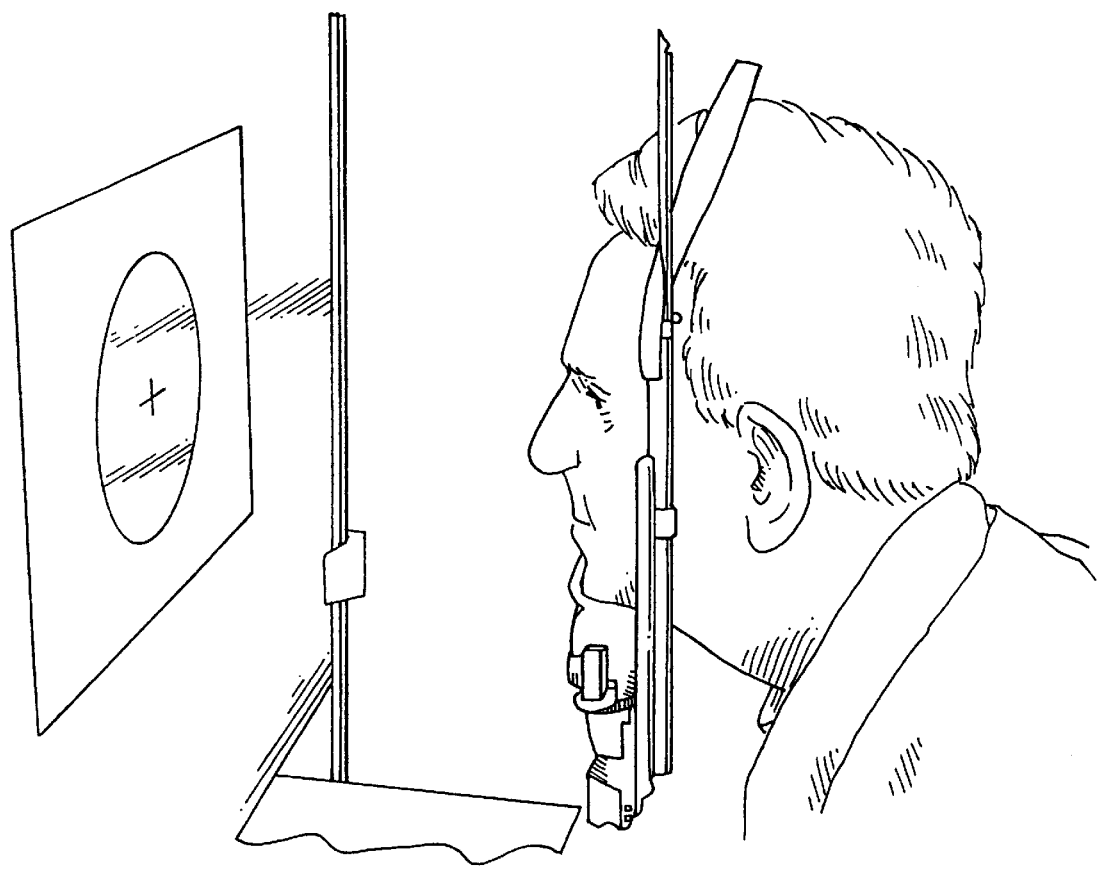
FIG. 1B is a representation showing a subject fixated on the screen of the perimeter of FIG. 1A.

Describing the present invention in greater detail, a high-resolution fundus perimeter was constructed using a laptop computer and a projector constituting a portable perimeter. The scheme of the overall arrangement of the perimeter is shown in FIG. 1A, and an example of a patient fixating on the screen is shown in FIG. 1B. As shown in FIG. 1(A) the main components of the perimeter are a laptop computer 10, a Liquid Crystal Diode (LCD) projector 12, and a fiberglass screen 14 on which appears a cross encompassed by a circle. The laptop is connected to the projector via a Red Green Blue (RGB) connection. FIG. 1(B) shows a subject 20 fixating on the screen 14. The subject's head is stabilized to eliminate involuntary movements. The cross surrounded by the circle projected onto or otherwise imposed on the screen 14 is the fixation target. As noted, the patient's head is stabilized in order to eliminate involuntary movements, and the operator is using the laptop to control the test procedure.

In a specific example, an IBM ThinkPad 600E laptop with an Intel Pentium-II MMX 300 MHz processor and 128 MByte memory was used. The projector was a NEC MT810G with a 600 ANSI lumens maximum light intensity, a more than 200:1 contrast ratio, and 800*600 dots resolution. The projector was located 83 cm horizontally from the screen, and displayed a picture that is 40 cm diagonally. With this arrangement, the luminance of the entire image remains uniform with little loss in intensity. The patient was seated close to the screen (about 20 cm) in order to retain the high and uniform brightness. The maximum visual field resolution that can be achieved under this setting is 0.12 minutes of arc (0.0020).

To calibrate the perimeter, the distance between the patient 20 and the screen 14 and the size of the picture (fixation target) on the screen 14 were set before the test began. Using these data, the perimeter can translate any desired visual field location to its corresponding pixels of the picture on the screen 14. The perimeter takes into account the eccentric fixation of the patient and the derived blind spot location. During the test, the patient was asked to adjust fixation on a cross, surrounded by circle (FIG. 1B), The circle, a feature of the present invention, was added to help patients with central scotoma who see a cross only faintly.

According to the invention two high-resolution mapping methods were developed, one static and one kinetic. In the former, a dot of light is flashed in random order in the tested visual field region, and the patient uses a dual-state switch to signal whether or not the flash was visible. It was found that a 300 msec flash is long enough to be perceived by low vision patients, yet short enough to eliminate significant eye movements of a watchful patient.[11] If the patient indicates that he did not see a specific flashed location, this location is flashed once again randomly later on. Only if the location was not seen in two attempts was it considered as being unseen. This method of the invention needs a relatively large number of flashes to cover the macular region. For example, to cover a circle of 8° radius, 197 locations are required to achieve 1° resolution, and 797 locations for 0.5° resolution, taking over one hour to complete.

To accelerate the test, an improvement to the standard static technique according to the invention was added. The test was started with relatively low resolution, and only the unseen zones were automatically remapped with improved accuracy, until the desired resolution was achieved. Using this improved aspect of the present invention, a multi-resolution static technique, an example of the result of two successive iterations is shown in FIGS. 2A and 2B. The first iteration, shown in FIG. 2A, maps a circle of 12° radius with resolution of 2°. The second iteration, shown in FIG. 2B, maps only the region of dots that were unseen in the first iteration. In greater detail, FIGS. 2A and 2B show an example of the result of two successive iterations of the multi-resolution static technique. The relevant statistics are presented below each iteration. FIG. 2A shows the first iteration, which consisted in mapping a circle of 12° radius and of 2° resolution. The 'X' denotes an unseen dot and the 'O' denotes a seen dot. FIG. 2B shows the second iteration, which consisted in mapping under double resolution only the dots which were unseen in the first iteration. The dots which had been seen in the first iteration are denoted by 'o'.

This test, which achieves the mapping of the 12° circle of 1° resolution, takes a total of about 19 minutes. Although the multi-resolution static technique, according to the present invention, shortens the test duration, mapping of the macula regions is still tedious, especially for an elderly patient who loses fixation control in a relatively short period. In addition, at this phase, only a supra-threshold test was used, as switching to a threshold test would have only extended the test duration. These shortcomings in the static method of the present invention served as the motivation to develop the kinetic technique of the present invention.

The basic problem confronted in the development of the method and apparatus of the present invention with a kinetic technique concerned the determination of the exact location of the moving dot when a patient signals its appearance/disappearance. Because, in the past, this problem was not resolved,[6,7] the clinical use of a computerized kinetic technique has not been used. However, through the development of the present invention, a solution to this problem has been worked out, and the technique employed by the invention, consists in determining the transition location by combining the patient's responses to two scanned lines at the same visual location, but with opposite directions of movement. An example of applying this aspect of the present invention is shown in FIG. 3. As shown in FIG. 3, the method for solving the response delay problem of the kinetic visual field mapping consists in scanning visual field locations in two opposite directions. The scanning can be effected by actually moving the light beam projected onto the screen, or by successively lighting adjacent areas or pixels of the screen. That is the successive lighting creates an apparent movement of the light. As shown in FIG. 3 schematically, the two upper lines having opposite moving directions, but represent the same visual field location. The displacements between the patient's signals in the left-to-right line and the corresponding signals in the right-to-left line are estimated as twice (*2) the response delay. The actual locations are determined halfway between each two corresponding signals as represented by the bottom third line. According to the present invention, the displacements between the patient's signals in the left-to-right motion and the corresponding signals in the right-to-left motion are estimated as caused by twice the response delay, and the actual transition locations are determined at the halfway point between the two corresponding signals. An algorithm was developed to enable the merging of corresponding opposite signals and to eliminate spurious signals. It was found that a scanning rate of 1.5°/sec to be optimal for low vision patients. In the method of the present invention, the lines and/or points of the visual field are scanned in random order. During each scan, the patient is asked to maintain a steady fixation.

Figure 4A:
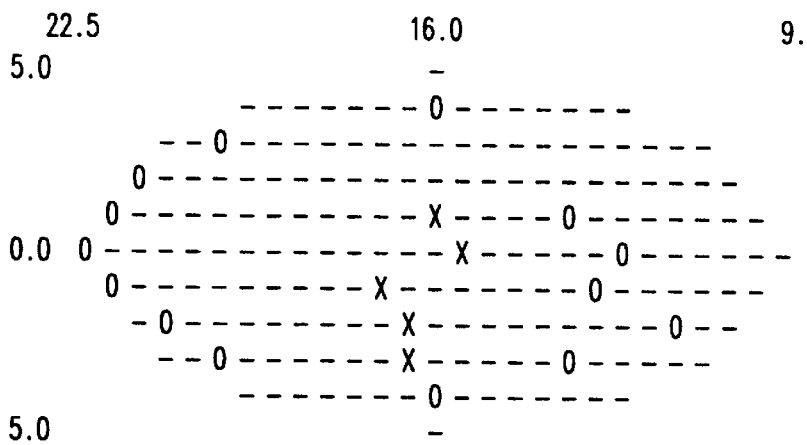
FIGS. 4A, 4B and 4C are schematic representations showing an example of a horizontal kinetic test over the blind spot of an intact retina with FIG. 4A showing a subject's raw data for left-to-right scans, FIG. 4B showing the subject's raw data for right-to-left scans and FIG. 4C showing the output of the merging algorithm of the present invention.
Figure 4B:
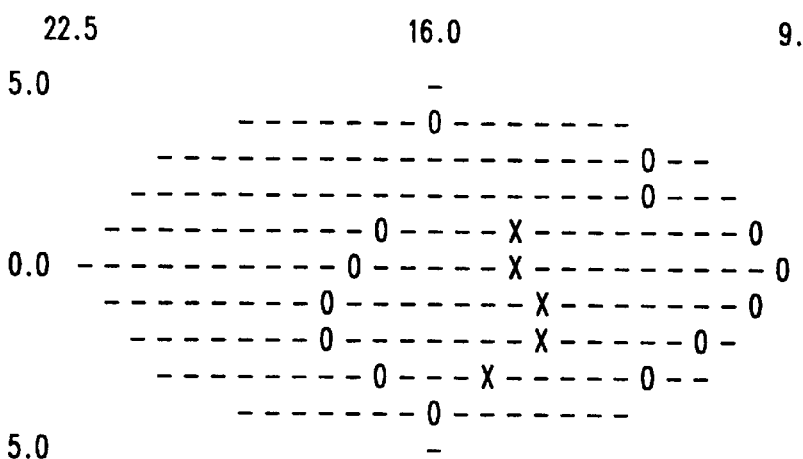
Figure 4C:
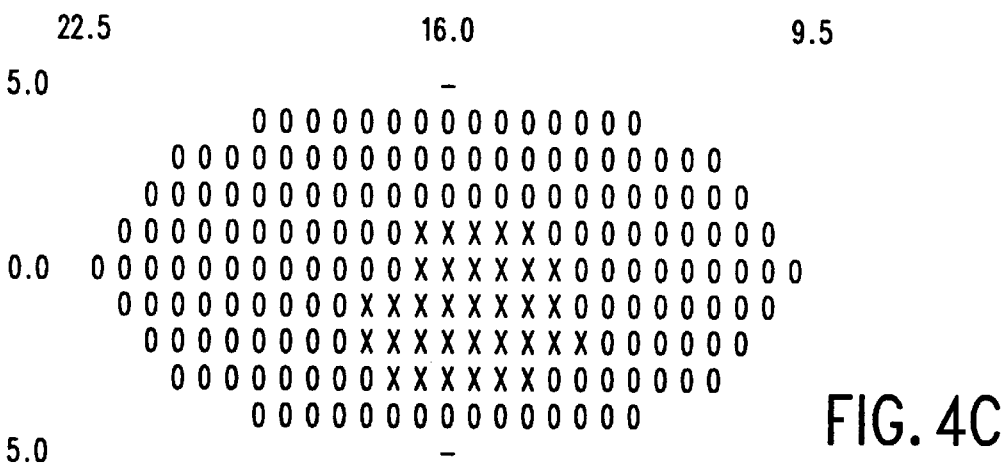

In addition, several flashes of dots are projected, which have a different color from the moving dot, to the blind spot. FIGS. 4A, 4B and 4C show an example of the result of the test over the blind spot of an intact retina. What is portrayed in these Figures is an example of the result of a horizontal kinetic test over the blind spot of an intact retina. FIG. 4A shows the subject's raw data for the left-to-right scans. 'O' denotes the signal where the patient started seeing, and the 'X' denotes the signal where the patient stopped seeing. FIG. 4B shows the subject's raw data for the right-to-left scans with the same notation as in FIG. 4A. FIG. 4C shows the output of the merging algorithm. The 'X' denotes unseen points and the 'O' denotes seen points.

All the scanned lines were horizontal. As noted above, FIG. 4A and FIG. 4B present the subject's raw data for the left-to-right scans and the right-to-left scans, respectively.

FIG. 4C shows the output of the merging algorithm. The horizontal resolution is defined only for presentation purposes since the scans are perceived continuously due to the apparent motion effect.[23] In general, one can choose a combination of horizontal, vertical or radial scans. It is more convenient to compare the results of the horizontal and vertical scan to the static mapping, but on the other hand, radial scans are perceived better.

As defined, a "seen point" in the kinetic test is a point that fell within a seen segment of the merged line, and in the static test, is a point that was seen at least once. In contrast, an "unseen point" in the kinetic test is defined as a point that fell in or occurs in an unseen segment of the merged line, and in the static test, as a point that was not seen after two attempts. In the static test, reference is made only to the map of the final phase. Using these definitions, one can define an "unseen region" as a region in which most of the points are unseen, and a "seen region" as region in which most of the points are seen. The border between these two kinds of regions is defined as the "mapping-border". The seen points in the unseen region and the unseen points in the seen region are defined as "inconsistent points".

Visualization of the results over the fundus image, which is photographed in advance, is performed offline for both techniques. Before testing a patient, the retinal fixation point is indicated, for example by using a slit lamp with a narrow red beam, according to known technology. After the test, and preferably, but not necessarily immediately, the operator should just insert the scale of the fundus image and identify the fixation point in it, and then, the mapping result is instantly visualized over the image.

Before testing AMD patients for the research purposes of the examples of the invention, the intact macula and the blind spot of four healthy subjects aged from 22 to 34 were tested, as a control. Since the macula and the blind spot region can be easily computed from the fundus image, and since the subjects could maintain good fixation during the test, these test results were used to confirm the validity of the inventive methods for seeing (macula) and unseeing (blind spot) regions. Four AMD male patients underwent several kinetic and static tests over their damaged region. The subjects and patients characteristics are outlined in table 1.

Figure 5A:
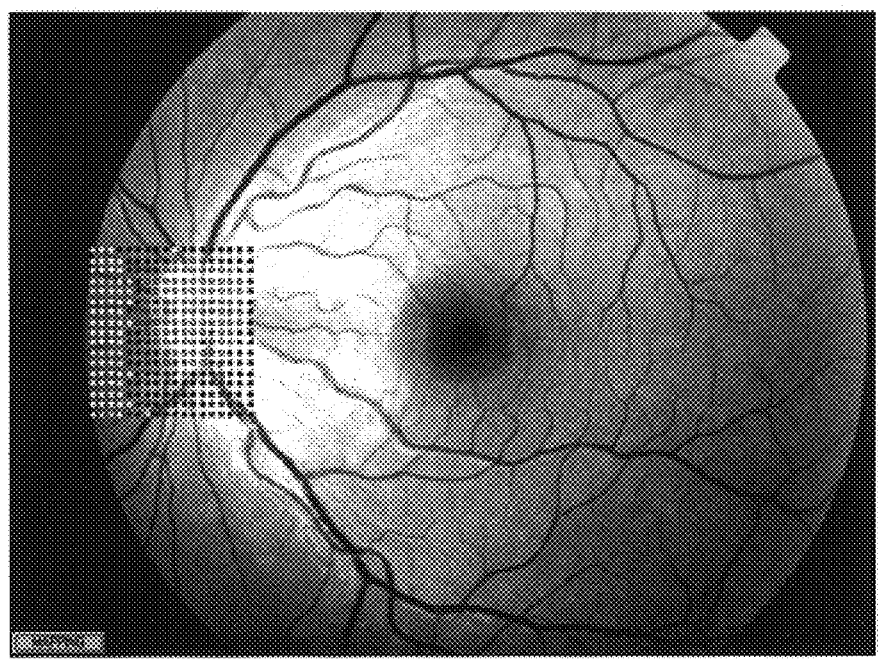
FIGS. 5A and 5B are schematic visualizations of the static and kinetic mapping, according to the present invention, over the blind spot of an intact retina of a patient.
Figure 5B:
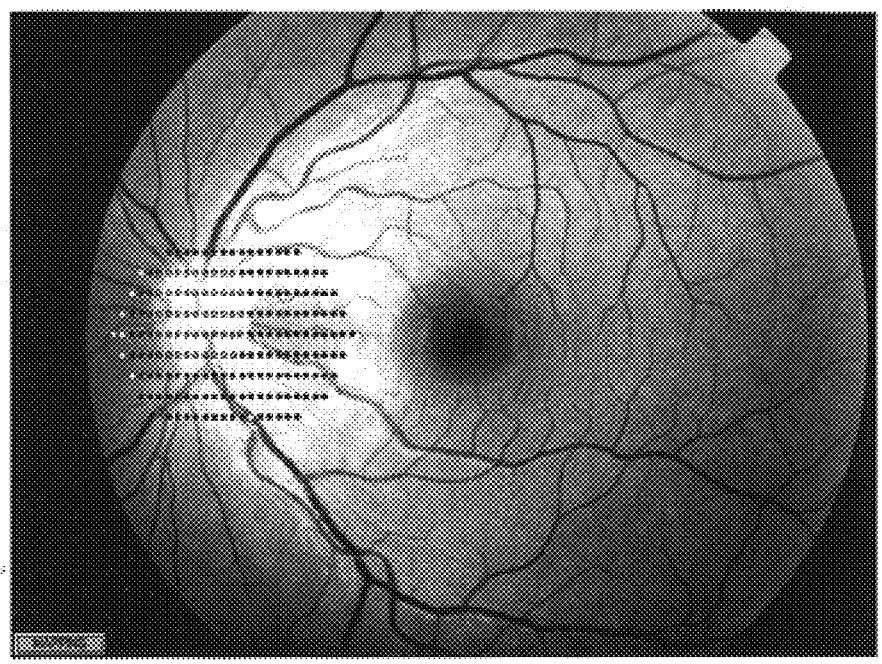

FIGS. 5A and 5B show an example of the visualization of the static mapping, FIG. 5A, and kinetic mapping, FIG. 5B, over the blind spot of the intact retina of subject #1. As is evident from the Figure, the mapping-border is congruent with the blind spot in both mapping methods. However, some inconsistent points are observable inside the blind spot region in the static mapping, while all the points are consistent in the kinetic mapping. The congruency of the mapping-border and the apparent border of the corresponding spot in the fundus image on the one hand, and the inconsistency of the static method on the other hand, are even more salient when mapping damaged retinas.

Figure 6A:
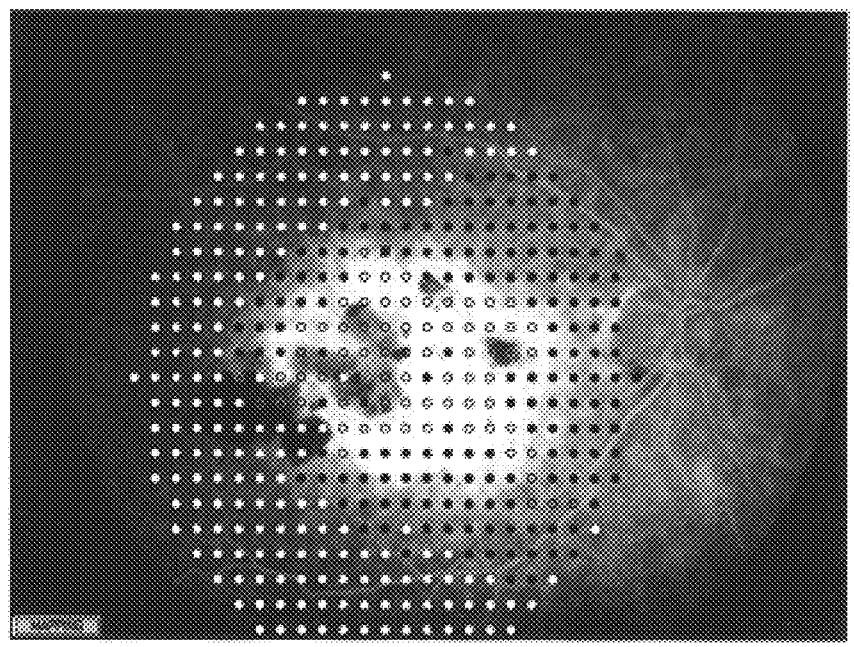
FIGS. 6A and 6B are schematic visualizations of the static and kinetic mapping, according to the present invention, over the damaged macula of a patient.
Figure 6B:
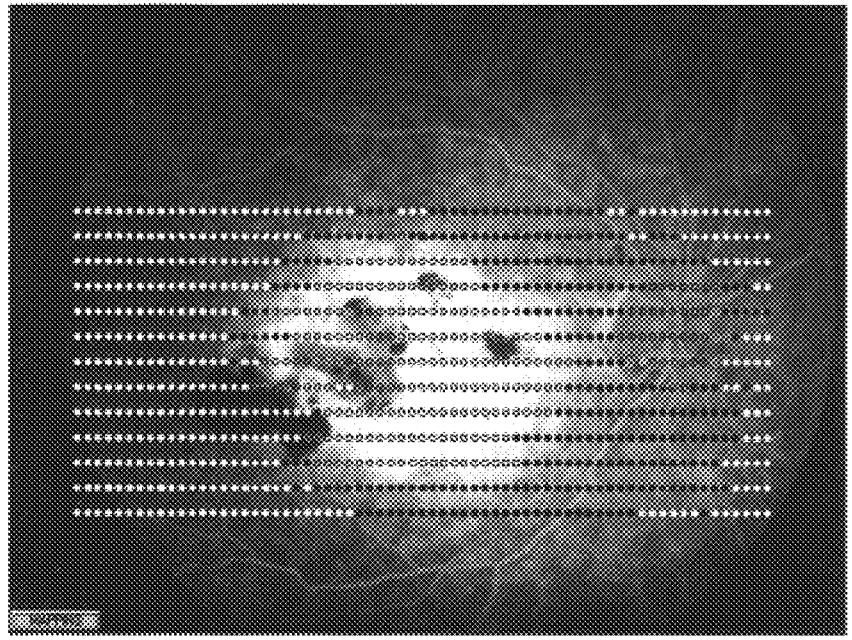

FIG. 6 shows representative results of the static, FIG. 6A, and the kinetic, FIG. 6B, tests for the damaged macular region of patient #5. In the kinetic test, there is good agreement between the mapping-border and the apparent border of the fundus image—the incongruent region size is less than 0.6 Disk Area (DA) while the scotoma size is 22 DA (less than 3% of incongruency)—and there is no inconsistency. The static test reveals poorer correspondence (7% of incongruency) with significant inconsistency at the center of the unseen region. Since repeatable static tests over the same region resulted in different inconsistent points inside the unseen region, a probable assumption one can make is that these inconsistent points occurred by random eye movements of the patient.

To analyze the influence of eye movements on the results, the error of an inconsistent point was computed as the distance of the point from its closest border point. The reason for measuring this distance is that an inconsistent point at distance d from its region border can be caused by eye movements of size d or larger. Thus, the average inconsistency error of a test is the average of the error of its inconsistent points. This computation takes into account merely the displacement of an inconsistent point from its closest border point, and not from its original location which is unknown. It also does not take into consideration eye movements that displace the test points but leaves them in their original seen or unseen region. However, it is believed that this measure indicates the tendency of the eye movements error, with some unavoidable variance.

FIG. 7 shows the inconsistency level of the two methods, and the relation between the inconsistency and visual acuity.

TABLE 1

Subject Characteristics

| Patient No., Age (yrs.), Sex | Diagnosis | Visual Acuity* | Scotoma size (DA[†]) | Distance of Fixation from the Fovea (mm) | Orientation of Fixation Relative to the Fovea (mm) |
|---|---|---|---|---|---|
| 1, 28, F | Healthy | 6/6 | N/A[‡] | N/A | N/A |
| 2, 22, M | Healthy | 6/6 | N/A | N/A | N/A |
| 3, 27, F | Healthy | 6/6 | N/A | N/A | N/A |
| 4, 34, M | Healthy | 6/6 | N/A | N/A | N/A |
| 5, 74, M | AMD[§] | 6/144 | 22 | 1.66 | Vertically above |
| 6, 75, M | AMD | 6/80 | 6 | 0 | N/A |
| 7, 76, M | AMD | 6/60 | 10 | 1.33 | Vertically under |
| 8, 71, M | AMD | 6/90 | 8 | 0 | N/A |

*The Snellen visual acuity
[†]DA = Disk area
[‡]N/A = Not applicable
[§]Scar stage AMD Perimeter was tested in a primary study that extended over a period of one year on eight subjects, four healthy of both sexes with intact retinas as a control, and four males with damaged retinas associated with AMD.

Figure 7B:
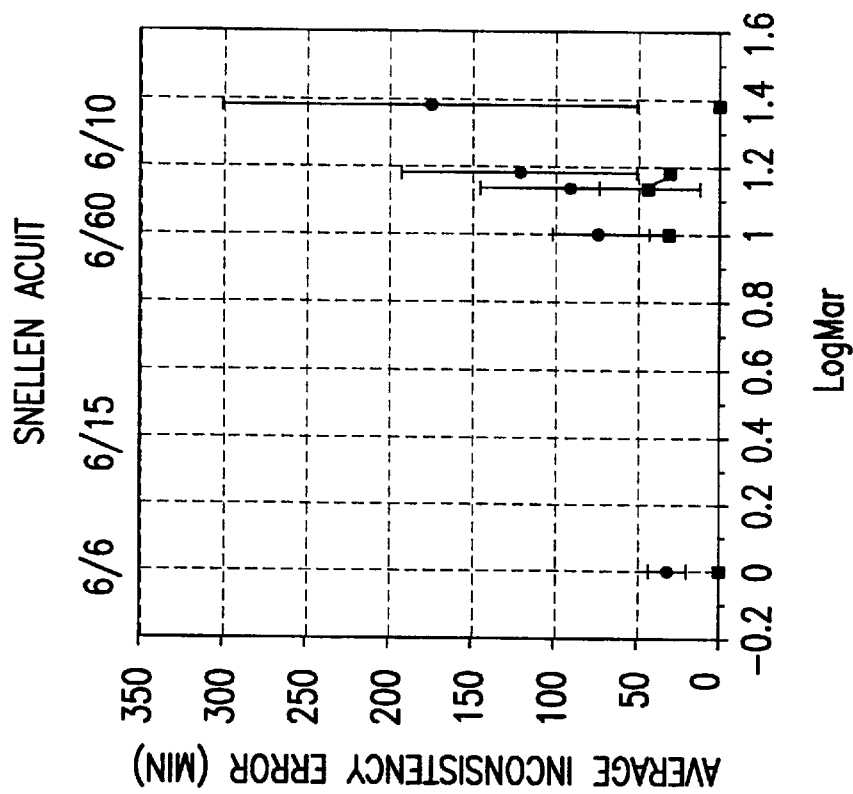
FIG. 7 is graphical representation of the percents of inconsistent point and average of inconsistency error versus visual acuity.
Figure 7A:
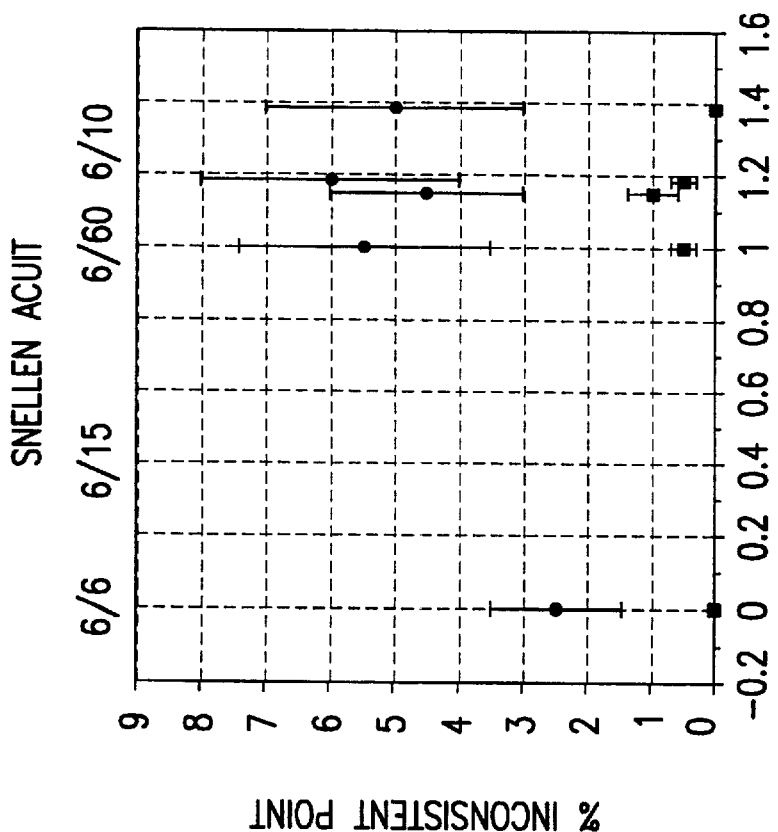

The graph in FIG. 7A demonstrates that the static method is less consistent than the kinetic method, since for each visual acuity, the static method has more inconsistent points. Applying a non-parametric Wilcoxon test, which assumes no prior knowledge of the distribution, yields a border significant difference between the static and the kinetic (p=0.0612). FIG. 7B reveals high correlation between the increase in the average inconsistency error of the static method and the decrease in visual acuity, 0.86 in the Pearson correlation (p=0.0617). This result is consistent with the known finding that the average minimal eye movements in the static test increases as the visual acuity decreases.[9]

The multi-resolution static test converges toward the unseen sub-regions, accelerating the duration of the standard static test. To measure this acceleration statistically, the total test duration was divided by the number of points that would be generated in the initial visual field region under the final resolution (which is the same as the initial resolution in fixed-resolution test). In more than thirty tests of each kind it was found that the average time per point in the common static test is 14.1 seconds compared with 3.6 seconds for the multi-resolution test, a saving of 75% in test duration. The kinetic test does not change with resolution, but its speed arises from its continuous mapping. To compare the duration of the kinetic and static tests, the duration of the kinetic test was divided by the number of points that would be generated by the static test over the same region and with the same final resolution. The average result of 25 tests was 2.6 seconds per point. It implies that most of the static test time is consumed by the fixation adjustment between the flashes. In addition, most of the subjects reported that the static test was more tedious. However, the kinetic test requires some training trials until the patient can maintain the fixation while the testing point is moving. In contrast, the patient can start the static test almost immediately and adjust fixation between the flashes.

During the kinetic test, the patients reported that some points were perceived with a degree of blur. This blur is probably a motion-related effect, and it suggests that the kinetic test is more sensitive than the static, since the response for the same constant stimulus level (supra-threshold screening level) is more graded—it differentiates between "see", "don't see" and "see blurly". In the foregoing studies, the patients were told to report the blurred perception as see or don't see. Using the supra-threshold test without considering the blurred perception, there was no finding of any consistent evidences for residual vision within the scotomas, although according to experience and knowledge about the patients, it was believed that some form of residual vision may be present. Residual vision is expected to be found as repeatable seen points in the unseen region, namely as inconsistent points in the unseen region that arise consistently in the same visual field location. However, it will be necessary to use more sensitive tests to explore the presence of residual vision. In the kinetic test, residual vision may also be revealed by blurred points.

The present invention provides a low-cost high-resolution perimeter with the ability to visualize the results over the fundus photograph. The low-cost implementation was accomplished by using off-the-shelf standard computer and projector equipment. In order to achieve the high-resolution requirement, the test must be accurate and sufficiently short. The high-resolution mapping was implemented by using two different methods. The first method is static in nature and, therefore, requires adjustment between each flash. The duration of this commonly used test was reduced by implementing a multi-resolution procedure. Although the test was considerably shortened, it does not avoid the tedious fixation effort required from the patient throughout such test. This continuing effort results in eye movements and inconsistent points which become more significant as the visual acuity of the patient decreases. To eliminate the error associated with eye movements and to accelerate the test, the invention implemented a second method, bi-directional kinetic. It was necessary to overcome the problem of unknown response delay by developing an appropriate merging algorithm. The kinetic test results better fit the scotomas in fundus photographs, were more consistent, and therefore, more repeatable, and usually shorter than the static test. However, the kinetic test required some training before the subject, especially the elderly, can maintain fixation and achieve consistent results.

In the kinetic test, several regions inside the scotomas were perceived with some blur, suggesting high sensitivity of this method. An improvement to this inventive method is to use threshold tests, because the kinetic method has high sensitivity. Although no confirmation for residual vision inside the scotoma was found, however, blurred regions could provide an evidence for some residual vision inside the scotoma.

Compared with the SLO method and apparatus, the present inventive method and apparatus are considerably less expensive, and can provide results that in practice approach those of the SLO. The most salient difference between the two apparatuses is their visualization technique. In the SLO, the visualization is done online, enabling detection and correction of eye movements. On the other hand, the techniques developed according to the present invention, enable rapid static mapping and accurate kinetic mapping, which minimize the influence of eye movements on the consistency of the results. In addition, as noted by Sunness and et al,[9] the SLO visualization is done over laser imaging, which is less familiar in the community, and raises difficulties in detecting atrophies, edemas and other types of retinal damage. In this sense, the present invention visualization has an advantage since it can be presented over different types of images, such as fundus photographs or angiography images.

As described in detail above, the inventive methods include a multi-resolution static method and a bi-directional kinetic method, for performing rapidly high-resolution accurate and repeatable visual field mapping, and the inventive apparatus includes a low-cost system for the purpose of carrying out the inventive methods. The invention can be used to detect and to follow the evolution of visual disorders caused by injury, stroke, disease, or other cause, from the first stages to the advanced levels, by screening or mapping the sensitivity, of any region in the visual field. The present invention overcomes the long duration problem of an accurate static test, and the accuracy problem of a rapid kinetic test, enabling rapid and accurate mapping by both types of tests. The time-efficiency of the disclosed inventive methods facilitates the fixation effort of the tested subject, and reduces the crucial influence of the eye movement error. The blur perception, which appears in the kinetic test, enables the performance of a high-sensitivity threshold test. For central field disorders, the methods of the invention enhance the fixation ability by using centralized peripheral fixation target, and take into account eccentric fixation by translating appropriately the tested region. The methods can be performed using the inventive apparatus comprising a small display screen, such as, a laptop computer, or with interactive local displays connected via a telemetric connection, like the Internet. The detection and correction of the eye movement is improved, by online tracking the subject pupil using a digital camera and tracking algorithm at the local site in accordance with known technology. Offline visualization of the mapping results is performed using known technology by automatically superimposing over the retinal photograph.

The main features of the present invention include rapid, accurate, and repeatable high-resolution visual field mapping (micro-perimetry) by using multi-resolution static mapping, bi-directional kinetic mapping or high-sensitivity bi-directional kinetic mapping. The inventive multi-resolution static mapping method includes the steps of flashing a dot of light at random locations in the tested visual field, fixation adjustment between each flash using a centrally presented target, detecting whether or not the patient sees the flash, by the patient signaling "see" or "not see". Essentially, the dot of light that is flashed is stepped from point to point, but not necessarily in order, but rather in random fashion. The method starts with relatively low-resolutions in a first phase, in order to rapidly obtain indications of the unseen regions, and with successive iterations remaps only the unseen regions under higher resolutions. The final results are presented with uniform resolution. Therefore, the highest tested resolution (regions which were tested merely with lower resolution are decomposed to the highest resolution, with the decomposed values being identical to the original value). Then, screening and threshold mapping takes place. In screening, only one intensity is used whereas in threshold mode, the intensity is varied from a low value to a high value to discover the threshold between "see" and "not see" for the intensity range. In the threshold mapping, the iterations are repeated for each tested intensity. Regions, which were unseen at higher intensity, or seen at lower intensity, are skipped. Acceleration is achieved by first testing with the lowest and highest intensities, and then testing with the intermediate intensities.

The bi-directional kinetic mapping method of the present invention includes the steps of moving a dot of light in lines at the tested visual field, maintaining patient fixation during each line scan, detecting Patient signals when the dot becomes visible or disappears, computing the patient's response delay by merging the patient's response to scans at the same visual location but with opposite scanning directions (each tested visual location is scanned with two opposite directions), determining the actual location of the patient's signal at a point between each two corresponding opposite signals (usually the halfway point). There are two types of presentation for the results obtained. In one form of presentation, "topographic lines" are derived showing the connecting lines of neighboring points of the obtained perceptual vision transition. In the other type of presentation which is called "discretization" and is a"static-like" presentation, the actual points with their perception values are presented. The movement of the dot of light and the mapping may be either rectilinear or polar (radial). The discretization presentation is usually in the form of a rectilinear display. The topographic lines produces a map of the transition between "see" and "not see" signals. The bi-directional kinetic mapping according to the invention, proceeds with screening and threshold mapping. The screening takes place using one selected intensity whereas for the threshold mapping, the scans are repeated for each tested intensity. Segments or points, which were unseen in higher intensity, or seen in lower intensity, are skipped. Acceleration is achieved by first testing with the lowest and highest intensities, and then testing with the intermediate intensities.

In accordance with an improved method of the invention, the high-sensitivity bi-directional kinetic mapping method comprises the step further steps of using three states of subject response, namely, "seen", "unseen", and "seen blurly", the last-mentioned response being between the first two, as explained in the foregoing. In addition two thresholds are attached to each tested region, one being the transition from "unseen" to "seen blurly", and the other being the transition from "seen blurly" to "seen".

Another feature of the present invention is the inclusion in the method and apparatus of a correction of the influence of eccentric fixation under central disorder. This is accomplished by finding, in advance, the eccentric fixation retinal point (for example by using slit-lamp and red laser beam, according to known technology), computing, in advance, the distance and orientation of the eccentric fixation point from the normal fixation point (the center of fovea), and displacing each tested location in the visual field by the computed distance and orientation.

Also, it has been discovered that using the normal fixation target of a cross in the center of the projection screen, it is difficult for a patient to maintain his/her concentration on the target, especially for a long period of time. According to the invention, the patient's fixation ability under central disorder can be sustantially enhanced and sustained using a centralized circle (or another centralized geometric (polygon) pattern) surrounding the fixation target, which may be a cross located in the center of the peripheral field of vision, but the invention may use only the circle without the central cross. The invention presents a circle (or another geometric (polygon) pattern—unbroken preferred, but may be broken) whose perimeter is located at the peripheral visual field and whose center is located at the center of the visual field (the fixation point). In the performance of the method without a central cross, the patient is asked to fixate on the center of the circle (unseen point) which is well estimated according to the periphery (the seen points).

In a still further development of the invention, online detection and correction of the influence of eye movements is effected by using a digital camera to watch the subject's eyes, with online tracking (using a computer including a microprocessor) of the pupils in the sequence of the eye's images to estimate the viewing direction of the subject relative to the desired fixation point. The output signals are fed to the computer-microprocessor to effect online displacement of the tested location in the visual field, according to the relative distance and orientation between the actual fixation point and the desired fixation point.

The methods of the invention utilize offline visualization of the mapping results over the retinal photograph using the computer-microprocessor by finding, in advance, the fixation retinal point (for example by using slit-lamp and red laser beam), scanning, in advance, the retinal photograph, into the computer, including its scale, signing the fixation point on the retinal computer image, offline graphical drawing of the test result over the retinal image, aligning it with the fixation point (the orientation is assumed to be fixed for all the subjects, since the patient's head is stabilized).

The invention provides display of the high-resolution test on a small screen by entering in a computer or microprocessor (which may include the display screen) in advance the measures (diagonal, or vertical and horizontal size) of the small display screen (for example, the laptop screen, or the image projected on a viewing screen), entering into the computer in advance the distance of the subject from the screen, calculating via the computer (offline or online), for each desired visual field location, the corresponding region on the screen, and online providing a Presentation of each visual field location at the appropriate region on the screen.

A still further refinement of the present invention is the implementation of the high-resolution test using interactive local displays connected via a telemetric connection, like the Internet. The method is carried out by the steps of separating the software to client and server modules, installing the client module software at a local computer where the patient will be tested, programming the client module software to be responsible for the display, and the interface with a subject patient, programming the client module software to use the local small screen for the display, programming the server module software to be responsible for the test planning, test management, and for storing and analyzing the results Of multiple tests according to the methods of the invention as described in the foregoing, and programming the server to connect via the telemetric connection with multiple clients, and interconnecting the server with multiple clients via a telemetric connection, preferably the Internet.

The invention also contemplates the online detection and correction of the eye movements of a patient undergoing test via a telemetric connection like the Internet by the steps of programming the client module software to use a local digital camera with which it is connected, and programming the client module software to be responsible for the online pupil tracking algorithm, and for the online detection and correction of the eye movements.

In another aspect of the invention, offline visualization via a telemetric connection like the Internet can be accomplished by the steps of scanning the retinal photograph of a patient at the local site to obtain a retinal image, sending the retinal image and its relevant data to the server for storing, and sending the retinal image to the local site upon request for visualization.

The invention provides high-resolution, accurate, repeatable and sensitive detection, follow-up and future estimation of the evolution of visual disorders, central or peripheral, with small (less than 1°) and big (couple of degrees) damaged regions, caused by injury, stroke, disease, or other cause, from the first stages to the advanced levels, by using the novel multi-resolution static mapping method, the novel bi-directional kinetic mapping method or the novel high-sensitivity bi-directional kinetic mapping method, or any combination of the above methods in any sequence.

The novel micro-perimeter apparatus of the present invention comprises the components described to effect multi-resolution static mapping, bi-directional kinetic mapping, high-sensitivity bi-directional kinetic mapping, correction of the influence of eccentric fixation under central disorder, presentation of a centralized circle (or another centralized geometric pattern) to enhance the fixation ability under central disorder, online detection and correction of the influence of eye movements, offline visualization of the mapping results over the retinal photograph, display of the high-resolution test on a small screen, interactive local displays connected via telemetric connection, online detection and correction of the eye movements via telemetric connection and offline visualization via telemetric connection. In addition, the apparatus utilizes computers including the usual input/output, memory and microprocessor, as well as servers and communication connections, as necessary, to transmit information from one point to another, as duly noted above. The programming of computers and communication gear from the description above would be readily apparent to one skilled in the art to implement the described functions.

REFERENCES

1. Stein H A, Slatt B J, Stein R M. *The Ophthalmic Assistant, Fundamental and Clinical Practice*. 5th ed. CITY: The CV Mosby Company; 1988:411–428.
2. Lieberman M F, Drake M V. *Computerized Perimetry, a Simplified Guide*. 2nd ed. CITY: Slack Incorporated; 1992:1–73.
3. Bengtsson B, Heijl A, Olsson J. Evaluation of a new threshold visual field strategy, SITA, in normal subjects. *Acta Ophthalmol*. 1998;76:165–169.
4. Bengtsson B, Heijl A. SITA FAST, a new rapid perimetric threshold test, description of methods and evaluation in patients with manifest and suspect glaucoma. *Acta Ophthalmol*. 1998;76:431–437.
5. Drum B. Hybrid perimetry: A blend of static and kinetic techniques. *App. Opt*. 1987;26:1415–1420.
6. Timberlake G, Mainster M, Webb R, et al. Retinal localization of scotomata by scanning laser ophthalmoscopy. *Invest Ophthalmol Vis Sci*. 1982;22:91–97.
7. Culahm L E, Fitzke F W, Timberlake G T. Spatial reproduction of scotoma mapping with and without fixation correction using SLO. [ARVO abstracts]. *Invest Ophthalmol Vis Sci*. 1982;33:S970.
8. Newell W F. Ophthalmology, principles and concepts. 5th ed. CITY: The CV Mosby Company; 1982:92–95.
9. Sunness J S, Schuchard R A, Shen N, Rubin G S, Dagnelie G, Haselwood D M. Landmark-driven fundus perimetry using the scanning laser ophthalmoscope. *Invest Ophthalmol Vis Sci*. 1995;36:1863–1873.
10. Wolf S, Toonen F, Schaaf A, et al. Light sensitivity and fixation stability in patients with subretinal neovascularization. . [ARVO abstracts]. *Invest Ophthalmol Vis Sci*. 1994;35:S1504.
11. Dagnelie G, Schuchard R. Fixation stability during perimetry: Analysis of SLO data collected in low vision observers. *Optom Vis Sci*. 1992;69(suppl):29.
12. Sunness J S, Bressler N M, Maguire M G. Scanning laser ophthalmoscope analysis of pattern of visual loss in age-related geographic atrophy of the macula. *Am J Ophthalmol*. 1995;119:143–151.
13. Mainster M A, Timberlake G T, Webb R H, et al. Scanning laser ophthalmoscopy; Clinical applications. *Ophthalmology*. 1982;89:852–857.
14. Loewenstein A, Sunness S, Bressler N M, Marsh M J, Juan E. Scanning laser ophthalmoscope fundus perimetry after surgery for choroidal neovascularization, *Am J Ophthalmol*. 1998;125(5):5–10.
15. Guyer D R, Sunness J S, Fine S L, et al. Idoipathic macular holes and cyst: A scanning laser ophthalmoscpe analysis. [ARVO abstracts]. *Invest Ophthalmol Vis Sci*. 1190;31:S464.
16. Timberlake G T, Van De Velde F J, Jalkh A E. Clinical use of scanning laser ophthalmoscope retinal function maps in macular disease. *Lasers light Ophthalmol*. 1989;2:211–222.
17. Sjaarda R N, Frank D A, Glaser B M, et al. Assessment of vision in idiopathic macular holes with macular microperimetry using the scanning laser ophthalmoscope. *Ophthalmology*. 1993;100:1513–1518.
18. Rohrschneider K, Becker M, Fendrich T, et al. Fundus perimetry using a scanning laser ophthalmoscope (SLO) with an automated threshold strategy. [ARVO abstracts]. *Invest Ophthalmol Vis Sci*. 1994;35:S2189.
19. Hudson H L, Frambach D A, Chong L P, et al. Structural/functional retinal mapping in ARMD with SLO microperimetry. [ARVO abstracts]. *Invest Ophthalmol Vis Sci*. 1994;35:S2146.
20. Fletcher D C, Schuchard R A, Livingstone C L, et al. Scanning laser ophthalmology (SLO) macular perimetry and applications for low vision rehabilitation clinicians. *Ophthalmol Clin N Am*. 1994;7:257–265.

21. Culahm L E, Fitzke F W, Timberlake G T, et al. Assessment of fixation stability in normal subjects and patients using scanning laser ophthalmoscope. *Clin Vis Sci.* 1993;8:551–561.
22. Sabetes N R, Crane W G, Sabates F N, Schuchard R A, Fletcher D C. Scanning laser ophthalmoscope macular perimetry in the evaluation of submacular surgery. *Retina.* 1996;16:296–304.
23. Ullman S. The interpretation of visual motion. 1st ed. Cambridge, Mass.: MIT Press; 1979.

Although the present invention has been described in terms of preferred embodiments, nevertheless changes and modifications will occur to those skilled in the art which do not depart from the spirit, scope and contemplation of the invention described herein. Such changes and modifications are deemed to come within the purview of the invention as claimed.

What is claimed is:

1. A multi-resolution static mapping method including the steps of:
   (a) flashing a dot of light at random locations in a tested visual field in which a patient is undergoing test,
   (b) adjusting fixation between each flash using a centrally presented target,
   (c) detecting whether or not the patient sees the flash, by the patient signaling "see" or "not see",
   (d) starting with relatively low-resolutions in a first phase, in order to rapidly obtain indications of unseen regions, and
   (e) with successive iterations remapping only unseen regions under higher resolutions.

2. The method of claim 1 wherein final results are presented with uniform resolution.

3. The method of claim 1 wherein intensity of the dot of light is fixed at one intensity.

4. The method of claim 1 wherein the steps of claim 1 are reiterated during which, the intensity of the dot of light is varied from a low value to a high value to discover the threshold between "see" and "not see" for the intensity variations.

5. The method of claim 4 wherein the iterations are repeated for each tested intensity with regions, which were unseen at higher intensity, or seen at lower intensity, being skipped.

6. The method of claim 5 including the further step of accelerating by first testing with the lowest and highest intensities, and then testing with the intermediate intensities.

7. A bi-directional kinetic mapping method including the steps of:
   (a) moving a dot of light in lines at the tested visual field,
   (b) maintaining patient fixation during each line scan,
   (c) detecting patient signals when the dot becomes visible or disappears,
   (d) computing the patient's response delay by merging the patient's response to scans at the same visual location, but with opposite scanning directions,
   (e) each tested visual location being scanned with two opposite directions, and
   (f) determining the actual location of the patient's signal at a point between each two corresponding opposite signals.

8. The method of claim 7 wherein results obtained are presented as "topographic lines" showing the connecting lines of neighboring points of the obtained perceptual vision transition.

9. The method of claim 7 wherein results obtained are presented "discretization" showing the actual points with their perception values.

10. The method of claim 7 wherein the movement of the dot of light and the mapping is one of rectilinear or polar.

11. The method of claim 7 including the further steps of screening and threshold mapping.

12. The method of claim 7 comprising the further steps of using three states of subject response, namely, "seen", "unseen", and "seen blurly", the last-mentioned response being between the first two.

13. The method of claim 12 wherein two thresholds are attached to each tested region, one being the transition from "unseen" to "seen blurly", and the other being the transition from "seen blurly" to "seen".

14. The method of claim 1 including the further steps of obtaining a correction of the influence of eccentric fixation under central disorder by finding, in advance, the eccentric fixation retinal point, computing, in advance, the distance and orientation of the eccentric fixation point from the normal fixation point, and displacing each tested location in the visual field by the computed distance and orientation.

15. The method of claim 7 including the further steps of obtaining a correction of the influence of eccentric fixation under central disorder by finding, in advance, the eccentric fixation retinal point, computing, in advance, the distance and orientation of the eccentric fixation point from the normal fixation point, and displacing each tested location in the visual field by the computed distance and orientation.

16. The method of claim 1 wherein the centrally presented target uses a centralized geometric pattern.

17. The method of claim 1 wherein the centrally presented target is a circle.

18. The method of claim 7 wherein the centrally presented target uses a centralized geometric pattern.

19. The method of claim 7 wherein the centrally presented target is a circle.

20. The method of claim 1 including the further steps of online detection and correction of the influence of eye movements is effected by using a digital camera to watch the subject's eyes, with online tracking of the pupils in the sequence of the eye's images to estimate the viewing direction of the subject relative to the desired fixation point, feeding the output signals are fed to the computer to effect online displacement of the tested location in the visual field, according to the relative distance and orientation between the actual fixation point and the desired fixation point.

21. The method of claim 7 including the further steps of online detection and correction of the influence of eye movements is effected by using a digital camera to watch the subject's eyes, with online tracking (using a computer) of the pupils in the sequence of the eye's images to estimate the viewing direction of the subject relative to the desired fixation point, feeding the output signals are fed to the computer to effect online displacement of the tested location in the visual field, according to the relative distance and orientation between the actual fixation point and the desired fixation point.

22. The method of claim 1 including the further steps of offline visualization of the mapping results over the retinal photograph using a computer by finding, in advance, the fixation retinal point, scanning, in advance, the retinal photograph, into the computer, including its scale, signing the fixation point on the retinal computer image, offline graphical drawing of the test result over the retinal image, and aligning it with the fixation point.

23. The method of claim 7 including the further steps of offline visualization of the mapping results over the retinal photograph using a computer by finding, in advance, the fixation retinal point, scanning, in advance, the retinal photograph, into the computer, including its scale, signing the fixation point on the retinal computer image, offline graphical drawing of the test result over the retinal image, and aligning it with the fixation point.

24. The method of claim 7 including the further steps of displaying the high-resolution test on a small screen by entering in a computer in advance the measures of a small display screen, entering into the computer in advance the distance of the subject from the screen, calculating via the computer, for each desired visual field location, the corresponding region on the screen, and online providing a presentation of each visual field location at the appropriate region on the screen.

25. The method of claim 7 including the further steps of using interactive local displays connected via a telemetric connection, by separating operative software to client and server modules, installing the client module software on a local computer where the patient will be tested, programming the client module software to be responsible for the display, and the interface with a subject patient, programming the client module software to a the local small screen for the display, programming the server module software on a server to be responsible for the test planning, test management, and for storing and analyzing the results of multiple tests, programming the server to connect via the telemetric connection with multiple clients, and interconnecting the server with multiple clients via a telemetric connection.

26. The method of claim 25 including the further steps of effecting online detection and correction of the eye movements of a patient undergoing test via a telemetric connection by programming the client module software to use a local digital camera with which it is connected, and programming the client module software to be responsible for the online pupil tracking algorithm, and for the online detection and correction of the eye movements.

27. The method of claim 25 including the further steps of offline visualization via a telemetric connection by scanning the retinal photograph of a patient at a local site to obtain a retinal image, sending the retinal image and its relevant data to the server for storing, and sending the retinal image to the local site upon request for visualization.

28. Micro-perimeter apparatus comprising:
(a) a device to produce a flashing a dot of light at random locations in a tested visual field in which a patient is undergoing test,
(b) a centrally presented target adjusting fixation between each flash,
(c) a detecting device for detecting whether or not the patient sees the flash, by the patient signaling "see" or "not see", and
(d) a controller connected to the detecting device and responsive thereto to obtain relatively low-resolutions in a first phase, in order to rapidly obtain indications of unseen regions, and with successive iterations remapping only unseen regions under higher resolutions.

29. Apparatus according to claim 28 wherein the device to produce a flashing dot of light is moved in lines at the tested visual field, and a computer computes the patient's response delay by merging the patient's response to scans at the same visual location, but with opposite scanning directions, each tested visual location being scanned with two opposite directions, and determines the actual location of the patient's signal at a point between each two corresponding opposite signals.

30. The apparatus of claim 29 wherein the movement of the dot of light is one of rectilinear or polar.

31. The apparatus of claim 28 wherein the detecting device provides three states of subject response, namely, "seen", "unseen", and "seen blurly", the last-mentioned response being between the first two.

32. The apparatus of claim 28 wherein a computer determines a correction of the influence of eccentric fixation under central disorder by finding, in advance, the eccentric fixation retinal point, computing, in advance, the distance and orientation of the eccentric fixation point from the normal fixation point, and displacing each tested location in the visual field by the computed distance and orientation.

33. The apparatus of claim 28 wherein the centrally presented target is a centralized geometric pattern.

34. The apparatus of claim 28 wherein the centrally presented target is a circle.

35. The apparatus of claim 28 including a computer and digital camera programmed for making online detection and correction of the influence of eye movements, the digital camera to watch the subject's eyes, with the computer receiving the output signals from the digital camera to effect online tracking of the pupils in the sequence of the eye's images to estimate the viewing direction of the subject relative to the desired fixation point, the computer effecting online displacement of the tested location in the visual field, according to the relative distance and orientation between the actual fixation point and the desired fixation point.

36. The apparatus of claim 28 including a computer programmed to effect offline visualization of the mapping results over a retinal photograph by finding, in advance, the fixation retinal point, scanning, in advance, the retinal photograph, into the computer, including its scale, signing the fixation point on the retinal computer image, offline graphical drawing of the test result over the retinal image, and aligning it with the fixation point.

37. The apparatus of claim 28 including a computer programmed to display the high-resolution test on a small screen by entering in advance the measures of a small display screen, entering into the computer in advance the distance of the subject from the screen, calculating via the computer, for each desired visual field location, the corresponding region on the screen, and online providing a presentation of each visual field location at the appropriate region on the screen.

38. The apparatus of claim 28 including computing equipment programmed for using interactive local displays connected via a telemetric connection, separate operative software loaded into client and server modules, the client module software installed on a local computer where the patient will be tested, the client module software programmed to be responsible for the display, and the interface with a subject patient, the client module software programmed to a local small screen for the display, the server module software programmed on a server to be responsible for the test planning, test management, and for storing and analyzing the results of multiple tests, the server programmed and connected via the telemetric connection with multiple clients, and the server interconnected with multiple clients via a telemetric connection.

39. The apparatus of claim 38 including a computer for effecting online detection and correction of the eye movements of a patient undergoing test via a telemetric connection by the client module software programmed to work with a local digital camera with which it is connected, and the client module software programmed to be responsible for the online pupil tracking algorithm, and for the online detection and correction of the eye movements.

40. The apparatus of claim 38 including the further steps of offline visualization via a telemetric connection by a device for scanning the retinal photograph of a patient at a local site to obtain a retinal image, a transmitter for sending the retinal image and its relevant data to the server for storing, and a transmitter for sending the retinal image to the local site upon request for visualization.

41. The treatment for a patient for obtaining high-resolution, accurate, repeatable and sensitive detection, follow-up and future estimation of the evolution of visual disorders, central or peripheral, with small and damaged regions, caused by injury, stroke, disease, or other cause, from the first stages to the advanced levels, comprising using a multi-resolution static mapping method including the steps of:

(a) flashing a dot of light at random locations in a tested visual field in which a patient is undergoing test, (b) adjusting fixation between each flash using a centrally presented target, (c) detecting whether or not the patient sees the flash, by the patient signaling "see" or "not see", (d) starting with relatively low-resolutions in a first phase, in order to rapidly obtain indications of unseen regions, and (e) with successive iterations remapping only unseen regions under higher resolutions.

42. The treatment for a patient for obtaining high-resolution, accurate, repeatable and sensitive detection, follow-up and future estimation of the evolution of visual disorders, central or peripheral, with small (less than 1°) and (couple of degrees) damaged regions, caused by injury, stroke, disease, or other cause, from the first stages to the advanced levels, comprising using a bi-directional kinetic mapping method including the steps of:

(a) moving a dot of light in lines at the tested visual field, (b) maintaining patient fixation during each line scan, (c) detecting patient signals when the dot becomes visible or disappears, (d) computing the patient's response delay by merging the patient's response to scans at the same visual location, but with opposite scanning directions, (e) each tested visual location being scanned with two opposite directions, and (f) determining the actual location of the patient's signal at a point between each two corresponding opposite signals.

43. The treatment for a patient according to claim 42 comprising the further steps of using three states of subject response, namely, "seen", "unseen", and "seen blurly", the last-mentioned response being between the first two.

* * * * *